United States Patent [19]

Hommel et al.

[11] Patent Number: 4,789,550

[45] Date of Patent: Dec. 6, 1988

[54] MICROCAPSULE COMPOSITION SUITABLE FOR CARDIOVASCULAR INJECTION

[75] Inventors: Martin Hommel, Toronto; Anthony Mein-Fang Sun, Willowdale; Mattheus F. A. Goosen, Toronto, all of Canada

[73] Assignee: Connaught Laboratories Limited, Willowdale, Canada

[21] Appl. No.: 631,471

[22] Filed: Jul. 16, 1984

[51] Int. Cl.$^4$ .................. A61K 9/22; A61K 9/24
[52] U.S. Cl. .................. 424/493; 424/490; 424/491; 424/497; 435/1; 435/178; 435/182; 435/180; 435/240.22
[58] Field of Search .......... 604/890, 891, 892; 424/21, 19, 491, 493, 497; 435/178, 182, 1, 240.22

[56] References Cited

U.S. PATENT DOCUMENTS

| | | | |
|---|---|---|---|
| 4,391,909 | 7/1983 | Lim | 435/178 |
| 4,407,957 | 10/1983 | Lim | 435/178 |
| 4,409,331 | 10/1983 | Lim | 435/178 |
| 4,543,332 | 9/1985 | Jao et al. | 435/180 |
| 4,673,566 | 6/1987 | Goosen et al. | 435/1 |
| 4,689,293 | 8/1987 | Goosen et al. | 435/1 |

*Primary Examiner*—Sam Rosen
*Attorney, Agent, or Firm*—Sim & McBurney

[57] ABSTRACT

Perfectly spherical, smooth and uniform microcapsules, which may contain living cells, are produced having a diameter less than 700 μm, e.g. 150 to about 500 microns, by employing an electrostatic droplet generator. A droplet is suspended from a pointed source, such as a needle, and is charged with high static voltage. A collecting vessel or ring device is charged with opposing polarity and attracts the droplet When a voltage potential threshold is passed, the droplet moves from the source to the collecting vessel. The voltage pulse height, pulse frequency and length, and extrusion rate of the droplet are adjustable so that predetermined sizes of droplets may be repeatedly generated and collected.

18 Claims, 2 Drawing Sheets

MICROCAPSULE COMPOSITION SUITABLE FOR CARDIOVASCULAR INJECTION

FIELD OF INVENTION

The present invention is concerned with droplet generation, particularly with respect to droplet generation in the encapsulation of living cells or individual cells in microcapsules.

BACKGROUND TO THE INVENTION

Various attempts have been made over the past twenty years to provide semi-permeable microcapsules which were both biocompatible with the body tissue and impermeable to the components of the immune system. Typical of such attempts is that described in U.S. Pat. Nos. 4,352,883 and 4,391,909 to Franklin Lim.

As set forth therein, living tissue or individual cells are suspended in an aqueous solution of a reversibly-gellable material, typically sodium alginate, and droplets of this suspension are allowed to drop into a hardening solution, typically calcium chloride. The temporary capsules so formed are then treated with polylysine and polyethyleneimine to form an outer semi-permeable coating. The core material is reliquified by ion-exchange of the calcium ions.

Survival times of microcapsules produced by this prior art procedure in the animal body were consistently less than 3 weeks, thereby severely limiting the utility of this prior art encapsulation procedure in the treatment of diseases requiring organ transplantation, such as diabetes and liver disease.

In copending U.S. patent application Ser. No. 501,445 filed June 6, 1983 (now U.S. Pat. No. 4,689,293 issued from a continuation of said serial number), assigned to the assignees hereof, the disclosure of which is incorporated herein by reference, there is described an improvement on the above-mentioned prior art procedure which forms a semi-permeable membrane which is both biocompatible and yet is able to protect transplanted tissue and cells from destruction by the immune system, such that, in animal tests, a single intraperitoneal transplant of encapsulated islets reversed the diabetic state for more than one year.

The success of the procedure according to the aforesaid application results from a semi-permeable and durable membrane which has an outer surface of biocompatible negatively-charged material. The improved durability, i.e. resistance to rupture, of these microcapsules is due to their near perfect spherical shape and enhanced capsule membrane thickness.

Although the microcapsules produced in the aforesaid pending application represent a significant advance in the treatment of diseases requiring organ transplantation, there is one drawback which inhibits more ideal utilization of the microcapsules and this drawback arises from the relatively large size of the individual microcapsules, which have a diameter from 700 to 1000 $\mu$m. Microcapsules produced according to the procedure of the Lim patents also had relatively large diameters of about 1000 to 2000 $\mu$m. Microcapsules having these diameters cannot be injected directly into the cardiovascular system, since they would occlude the blood vessel. Accordingly, the microcapsules must be implanted into large body cavities, such as the intraperitoneal cavity.

Location of the implants in an area of the body other than the cardiovascular system results in an increase in the response time of the microcapsules to changing blood conditions, since the microcapsules are not directly in contact with the blood stream. In addition, the relatively large size of the microcapsules compared to the microencapsulated tissue or cells (e.g. about 200 $\mu$m for islets of Langerhans) results in a high diffusional resistance for molecules passing through the microcapsule core.

An air jet-syringe pump extrusion method was used in the procedure of the aforementioned pending application and in the Lim patents to product gel droplets containing entrapped islets, or other tissue or cells, from the suspension of the islets in aqueous sodium alginate solution. In this procedure, the sodium alginate solution is extruded through a needle located inside a sheathed tube through which air flows at a controlled rate. As liquid droplets are forced out of the end of the needle by the syringe pump, the droplets are pulled off by the shear forces set up by the rapidly-flowing air stream. The higher the volumetric air flow rate, the stronger are the shear forces, the more quickly the droplets are pulled off the end of the needle and the smaller are the resultant droplets.

However, there are inherent restraints in this prior art procedure which prevent the size of microcapsule produced thereby being less than 700 microns. These restraints are that the viscosity of the gel-forming liquid must be greater than 30 cps in order to form perfectly spherical capsules, the minimum internal diameter of the needle must be greater than 300 $\mu$m (24 gauge) so as to prevent blockage of the needle by the islets, and the volumetric air flow rate must remain below 2000 cc/min in order to produce capsules of uniform diameter.

SUMMARY OF INVENTION

We have now discovered an improved procedure and apparatus for forming perfectly spherical, smooth and uniform droplets, such that there can be produced therefrom perfectly spherical, smooth and uniform microcapsules having a diameter of less than 700 $\mu$m, preferably about 150 to about 500 $\mu$m. Such microcapsules constitute one aspect of the present invention.

The novel microcapsules are formed of biocompatible material and contain living tissue or cells as a core material. A preferred core material is islets of Langerhans, so as to effect long term control of blood sugar levels in diabetic animals, including humans, by cardiovascular injection of biocompatible microencapsulated islets of Langerhans.

The provision of smaller diameter microcapsules in accordance with this invention, for example 200 to 300 $\mu$m, permits direct injection of the microcapsules into the blood stream, so that they may eventually lodge inside body organs, such as the liver or spleen, where they are continuously washed with fresh blood. The direct contact between the microcapsule and the blood significantly decreases the response time of the encapsulated tissue or cells to any biochemical change and thereby increases its efficiency. In addition, the smaller microcapsules result in a lower diffusional resistance for molecules passing through the microcapsule core, further increasing the efficiency of the cells. As a result, fewer of the smaller diameter microencapsulated islets of Langerhans need to be transplanted per kilogram of recipient body weight to achieve prolonged control of blood sugar levels in diabetic patients.

The living tissue-containing microcapsules also may be injected or implanted into any other convenient location in the body to be treated thereby, although this manner of administration is less preferred for the reasons noted above.

The small diameter microcapsules provided in accordance with this invention are formed by employing an electrostatic droplet generator in the initial gel-droplet-forming step. In this procedure, which constitutes a second aspect of the invention, a droplet, suspended from a source, is charged with a high static voltage and a second location, for example, a collecting vessel, is charged with opposite polarity, so as to attract the droplet. When a threshold of voltage difference between the locations is passed, the droplet moves from the source towards the second location and, thereby, to the collecting vessel.

An adjustable high voltage pulse is generated and applied to the droplet formed on the end of a needle by a syringe pump. The height of the voltage pulse, the pulse frequency and the pulse length are synchronized with the amount of material dispensed, so that known sizes of droplets can be repeatedly generated and collected.

DESCRIPTION OF PREFERRED EMBODIMENTS

Figure 1:
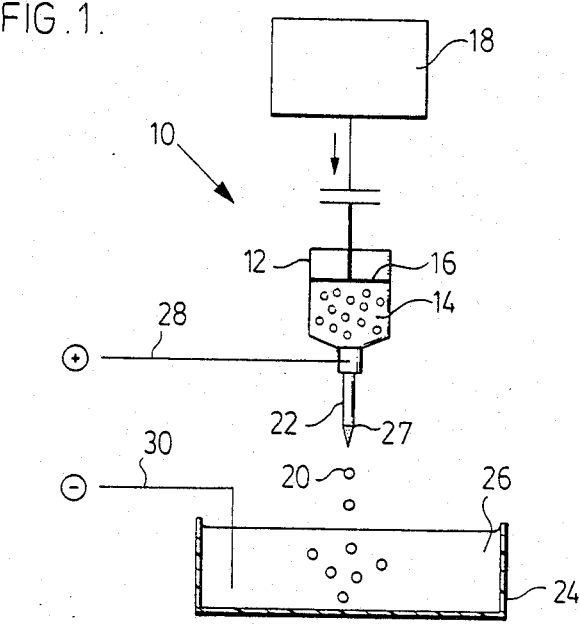
FIG. 1 is a schematic representation of a droplet-forming generator constructed in accordance with one embodiment of the invention.

Referring to the drawings, FIG. 1 shows a droplet-forming apparatus 10 constructed in accordance with one embodiment of the invention. As shown therein, a syringe 12 of non-conducting, usually polymeric, material contains a gel droplet-forming liquid 14 which contains living cells. A plunger 16 is driven by a syringe pump 18 to expel droplets 20 from the lower end of a stainless steel syringe needle 22 communicating with the lower end of the syringe reservoir 12, towards a collecting vessel 24 containing a hardening solution 26, which may be aqueous calcium chloride solution in the case of an aqueous droplet-forming liquid containing sodium alginate.

The positive lead 28 of an electrical pulse generator (see FIG. 3) is connected to the needle 22 while the negative lead of the pulse generator is connected to the hardening solution.

The needle 22 may be bevelled at its outlet tip 27, if desired. The tip 27 is located at a specific distance from the top of the recipient medium 26 in the collecting vessel 24 consistent with the voltage pulse to be applied therebetween to effect droplet formation. The size of the droplets 18 may be varied by varying the distance between the needle tip 27 and the liquid in the collecting vessel 24, with shorter distances leading to smaller droplets, by varying the voltage applied by the leads 28 and 30 with increased voltage leading to smaller droplets, by varying the pulse length of applied electricity with decreasing pulse length leading to smaller droplets, or by varying the speed of the pump 18 with decreasing pump speed leading to smaller droplets.

Figure 2:
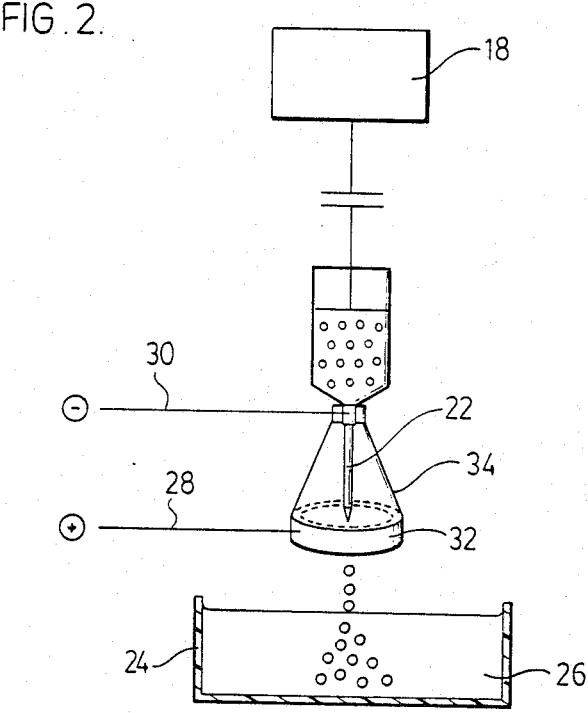
FIG. 2 is a schematic representation of a droplet-forming generator, constructed in accordance with a second embodiment of the invention.

FIG. 2 illustrates an alternative arrangement wherein the positive wire 28 from the pulse generator is detached from the needle 22 and instead is attached to a stainless steel ring 32 which is mounted to the lower end of a conical support 34 of non-conductive material which surrounds and extends below the needle 22. The negative lead 30 is attached to the needle 22 rather than to the recipient medium 26. In this arrangement, the distance between the tip 27 of the needle 22 and the top of the recipient medium 26 does not affect the gel droplet size.

The static voltage which is applied by lead wires 28 and 30 during droplet formation in FIGS. 1 and 2 results in gel droplets having a diameter less than about 700 $\mu$m, preferably about 150 to about 500 $\mu$m. These droplets then may be coated with a thin coating of a semipermeable biocompatible membrane. The resulting microcapsules are small enough to be injected into an animal body using an 18 gauge needle fitted to a syringe.

Since the voltage applied during droplet formation is a static one, the viability of encapsulated living tissue, such as islets of Langerhans or liver cells, is not destroyed, and hence the microencapsulated living tissue is capable of on-going metabolism.

Figure 3:
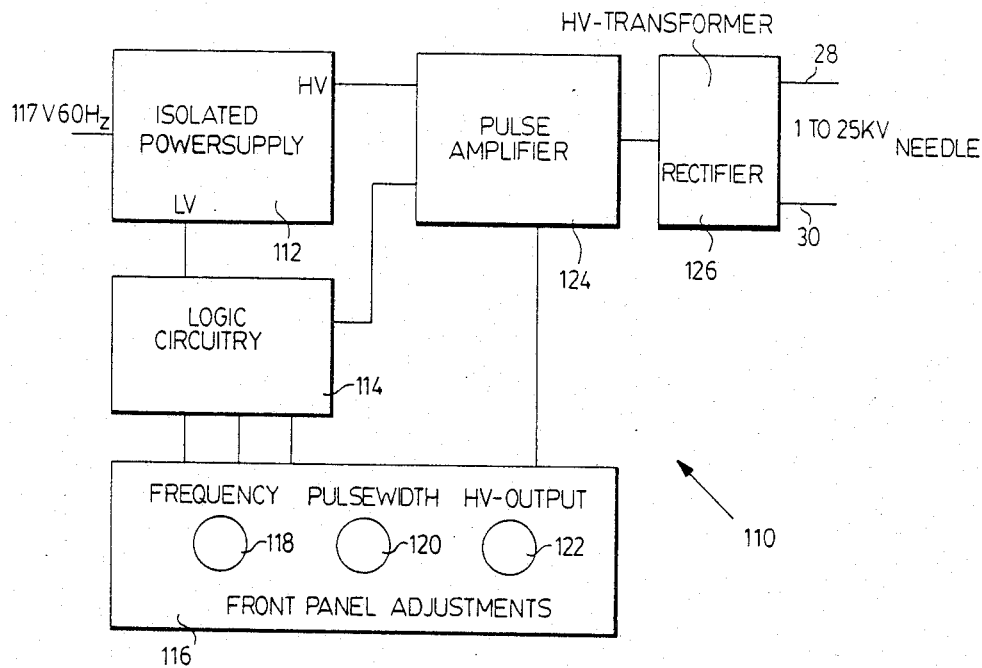
FIG. 3 is a schematic block diagram representation of the circuitry required to apply electricity to the droplet generator of FIGS. 1 or 2.
Figure 4:
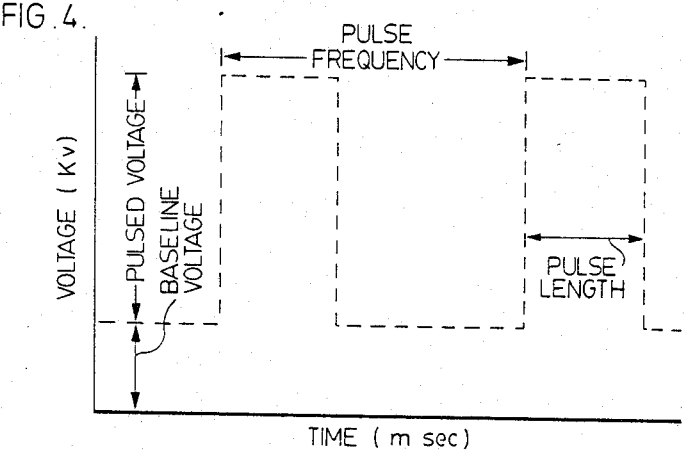
FIG. 4 is a graphical representation of a typical waveform of the output of the droplet generator circuitry of FIG. 3.

Referring now to FIGS. 3 and 4 of the drawings, an electrostatic pulse generator 110 suitable for formation of electrostatic pulses to be applied during droplet formation by the apparatus of FIG. 1 or 2 is illustrated in FIG. 3. As seen therein, the pulse generator 110 includes an isolated power supply 112, which may be connected to any desired source of electric power, logic circuitry 114, console panel 116 having adjusting knobs for pulse frequency 118, pulse width 120 and high voltage output 122, a pulse amplifier 124, and a high voltage transformer and rectifier 126 which outputs to the electrical lead wires 28 and 30.

The electrical pulse voltage, pulse frequency and pulse length which pass to the droplet forming apparatus 10 by the lead wires 28 and 30 may each vary widely, depending on the size of droplets desired. The pulse voltage, which determines the strength of the force pulling the droplets from the end of the needle 22, usually varies from about 1 to about 25 KV. The pulse frequency, which determines how many pulses are applied to the droplet, usually varies from about 10 to about 100 sec$^{-1}$. The pulse length, which determines the length of time for which the droplet-forming force is applied, usually varies from about 1 to about 6 m. sec. The interaction of the various time periods and their meaning is further illustrated in FIG. 4. These values are synchronized with the amount of material dispensed from the needle to obtain uniformly-sized droplets.

These specific design parameters ensure that there is no voltage overlap since a pulse lasts for 1 to 6 m. sec with each pulse occurring every 10 to 100 m. sec. Accordingly, a minimum of 4 m. sec and a maximum of 99 m. sec occurs between pulses. There is, in addition, a low baseline voltage which maintains the forming droplet in position between pulses.

There are numerous examples in the prior art of devices for electrostatically sorting biological cells, electrostatic sprays for dispensing paints and/or polymers and electrostatic droplet generators for ink printing. Illustrative examples of such devices are described in U.S. Pat. Nos. 4,347,935, 4,395,716 and 4,097,373 and British Patent No. 1,346,301. The droplet generators described in these prior patents use an external excitation source, such as acoustic vibration, for the initial formation of the droplet. The droplets are charged electrostatically only after they leave the generator, while in the present invention, the droplet-forming liquid 14 is charged directly by high static voltage. In the prior art arrangements, the external vibrating source causes formation of the droplets while in the present invention droplets are produced by direct electrostatic interaction.

The droplet generator of this invention is capable of producing very small, spherical droplets containing living cells with each step of the droplet formation being under the direct control of the operator.

Although the disclosure herein is directed mainly to the encapsulation of living tissue or cells for the specific purposes and advantages outlined above, it will be understood that the electrostatic droplet forming method and apparatus described herein has application in other fields and, for example, may be used in spray painting and ink printing.

GENERAL DESCRIPTION OF MICROENCAPSULATION

In this invention, living tissue or individual cells are encapsulated in a biocompatible semi-permeable membrane, in the form of a hydrogel. The material to be encapsulated is suspended in a physiologically-compatible medium containing a water soluble substance which can be reversibly gelled to provide a temporary protective environment for the tissue. The medium is formed into droplets containing the tissue, using the droplet generation procedure of the invention, and gelled, for example, by changing conditions of temperature, pH or ionic environment, to form temporary capsules, of substantially perfect spherical shape. Thereafter, the temporary capsules which result are treated to form a membrane of controlled permeability and negatively-charged outer surface about the shape-retaining temporary capsules. The semi-permeable nature of the membrane permits nutrients and oxygen to flow to the core material and metabolic products to flow therefrom while retaining the core material within the microcapsule. The biocompatible nature of the semi-permeable membrane allows the passage of such materials to and from the core to occur without inflammation or other adverse body response while the outer negatively-charged surface inhibits surficial cell growth, so that the membrane remains semi-permeable and effective for extended periods of time, typically from three to six months or longer.

The temporary capsules may be formed from any non-toxic water-soluble substance that can be gelled to form a shape retaining mass by a change of conditions in the medium in which it is placed, and also comprises plural groups that are readily ionized to form anionic or cationic groups. The presence of such groups enables surface layers of the capsule to cross-link to produce a permanent membrane when exposed to polymers containing multiple functionalities of the opposite charge.

Preferably, the temporary capsules are formed from a polysaccharide gum, which may be natural or synthetic, of a type that can be gelled to form a shape retaining mass by exposure to a change in conditions and can be permanently cross-linked or hardened by polymers containing reactive groups, such as amino groups, which can react with the acidic polysaccharide constituents. Most preferably, the gum is alkali metal alginate, specifically sodium alginate, although other water-soluble gums may be used.

The temporary capsules may be formed from sodium alginate by extruding droplets of aqueous sodium alginate solution into an aqueous calcium chloride solution. It is preferred that the temporary capsules be substantially spherical so that perfectly spherical microcapsules can be formed for cardiovascular injection. Substantially perfectly spherical temporary capsules are formed by using an aqueous sodium alginate solution having a viscosity of at least about 30 centipoise. At viscosities below this critical lower limit, the temporary capsules have an irregular shape. Perfectly spherical capsules are obtained over a wide range of viscosity of the sodium alginate solution above the critical lower limit of 30 centipoise, with an upper limit being dictated largely by the ability to extrude the solution into the hardening medium. However, it has also been found that the minimum size of perfectly spherical droplet which can be obtained at a viscosity of at least about 30 cps increases with increasing viscosity.

Formation of the permanent semi-permeable membrane about the temporary capsules preferably is effected by ionic reaction between free acid groups in the surface layer of the gelled gum and biocompatible polymers containing acid-reactive groups, such as, amino groups, typically in a dilute aqueous solution of the selected polymer.

The cross-linking biocompatible polymers which may be used include polyamino acids, preferably polylysine. It is noted that polyethyleneimine and other imine-containing polymers are unsuitable for membrane formation in view of their non-biocompatible nature. The molecular weight of the preferred polylysine polymer should be controlled within a narrow range of about 10,000 to about 30,000, preferably about 17,000, to achieve the required membrane porosity. The use of polylysine or other polyamino acid results in microcapsules having a positively-charged surface, which would be unsuitable for long term viability, although the microcapsules are biocompatible. It is important for long term in vivo life for the polylysine or other polyamino acid to be reacted for a period of time sufficient to develop a substantial thickness of membrane, so as to provide a substantial number of surface groups for post-reaction, as discussed below, sufficient structural strength to permit in vivo injection and sufficient quantity of biocompatible polymer to permit in vivo structural integrity to be retained. Usually, for polylysine of the molecular weight range noted above, a reaction time of at least six minutes is required to achieve these results, preferably at least about nine minutes, generally up to about 9 minutes. These reaction times result in a polylysine layer thickness of about 5 microns.

Surprisingly, the actual strength of the aqueous solution of polylysine used to react with the temporary capsules does not affect the capsule wall thickness, at concentration levels in excess of about 0.05 wt. %.

The semi-permeable membrane formed about the temporary capsules by the reaction with the polyamino acid next is treated with a non-toxic biocompatible water-soluble polymeric material which is capable of ionic reaction with free amino groups to form an outer negatively-charged coating about the membrane, typically by suspension of the microcapsules in an aqueous solution of the polymeric material. The material used to form the outer coating preferably is the same material as is used to form the temporary capsules, preferably a polysaccharide gum, more preferably an alkali metal alginate, such as, sodium alginate. Other biocompatible polymeric materials containing base-reactive groups, such as, polyvinyl alcohol and poly beta-hydroxy butyric acid, may be used to form the outer coating to the microcapsules. Molecular weights of such polymeric materials typically vary from about $10^4$ to about $10^6$.

The biocompatible water-soluble polymeric material containing amino-reactive groups reacts with the outer amino-groups of the semi-permeable membrane to form an outer coating. This outer coating permanently shrouds the polyamino acid layer, although leaving intact the porosity of the semi-permeable membrane, and provides a negatively-charged surface. By virtue of the number of surface amino groups on the polyamino acid membrane, resulting from the prolonged reaction time, the outer negatively-charged polymer coating resists degradation and removal, in vivo, so that the positively charged surfaces are not exposed to the body environment.

The treatment of the polyamino microcapsules with the biocompatible base-reactive material retains the overall biocompatible nature of the semi-permeable membrane and results in a negatively-charged outer surface which inhibits cell growth and, therefore, permits the semi-permeable membrane to retain its permeability and hence effectiveness over an extended period of time.

Following formation of the microcapsules, reliquification of the suspending medium for the core material may be effected by re-establishing the conditions under which the material is liquid. This may be achieved by ion exchange to remove multivalent cation, for example, by immersion in phosphate buffered saline or citrate buffer. The reliquification step, though beneficial in decreasing diffusion resistance, is not essential for the provision of an effective product and may be omitted, since it has been shown that transplanted islets (rat to mouse) in microcapsules whose interiors have not been reliquified, are also effective in normalizing blood sugar levels of diabetic animals. Surprisingly, the calcium alginate gel core does not reliquify inside the body, since intact gel cores have been found in microcapsules recovered from diabetic animals up to one year after implantation.

The process of the invention may be used to encapsulate living tissue, multicellular fractions thereof or individual cells, for example, islets of Langerhans, liver cells and red blood cells, and other biologically-active material. The microcapsules which result may be implanted into an appropriate site within a mammalian body for the purpose of providing the body with the specialized physiological function of the tissue while the tissue remains viable. The implantation may be achieved by simple injection, so that surgical procedures are not required. As noted earlier, cardiovascular injection may be effected, in view of the smaller diameter microcapsules which result from the electrostatic droplet generation procedure.

The core of the microcapsules contains the living tissue cells and an aqueous medium of nutrients sufficient to maintain the tissue and allow its normal metabolism. The cells are viable, physiologically active and capable of ongoing metabolism.

The biocompatible semi-permeable membrane encapsulating the core material consists of interpenetrating layers of ionically-interacted biocompatible materials. The overall wall thickness of the semi-permeable membrane usually varies from about 4 to about 6 $\mu$m. The microcapsules themselves have a diameter in the range of less than about 700 $\mu$m, preferably in the range of about 150 to about 500 $\mu$m for microcapsules containing islets of Langerhans as the core material. The biocompatible semi-permeable membrane is in the form of a hydrogel and hence has an overall water content within the membrane structure of at least about 20 wt %, which may vary up to about 95 wt %, depending on the molecular weight of the polyamino acid.

In a particularly preferred embodiment of the invention, living cells are microencapsulated within a polylysine-alginate semi-permeable hydrogel. The cells are initially suspended uniformly in a sodium alginate solution in physiological saline. Where the microcapsules are to be used for the treatment of diabetes by controlling blood sugar in animals, including humans, the living cells take the form of islets of Langerhans from an animal pancreas.

Spherical droplets containing the cells are produced from an aqueous sodium alginate solution by the electrostatic droplet generation procedure of the invention and are collected as gelled spheres in a hardening solution, such as, calcium chloride. The gelled spheres are coated with polylysine followed by an outer coating of sodium alginate. The microcapsules may then be suspended in isotonic sodium citrate or other convenient ion exchange medium to reliquify the alginate gel inside the microcapsule to restore the cells to a mobile state. As noted earlier, this step may be omitted, if desired.

The outer biochemically inert but biocompatible alginate surface is a negatively charged hydrogel containing up to about 95% water. The low interfacial tension between the swollen gel surface and the aqueous biological environment minimizes protein interaction, otherwise a strong protein-polymer interaction may cause a severe inflammatory response. The biocompatibility of the hydrogel membrane leads to long term viability of the capsules when implanted. Polyethyleneimine-surfaced microcapsules do not appear to possess this property, since they produce a strong inflammatory response and hence are rejected by the body, which severely limits the useful in vivo life of the microcapsules. The soft rubbery consistency of most hydrogels may also contribute to their biocompatibility by decreasing frictional irritation to surrounding tissues.

The strength of the microcapsules may be increased by additional cross-linking, for example, using glutaraldehyde, prior to reliquification of the gel, if effected.

For in vivo implantation, it is not essential that the biocompatible outer surface be composed of sodium alginate, but it is essential that the outer surface be biocompatible and negatively-charged. Binding occurs between the negatively-charged groups, usually hydroxyl or carboxyl groups, of the biocompatible outer surface material, and the positively-charged amino groups on polylysine.

By the present invention, therefore, there have been obtained biocompatible microcapsules capable of long term in vivo life and having a diameter which render them suitable for injection of living tissue into the blood stream, so that the microcapsules may lodge inside body organs for ongoing metabolism therein. While the primary benefit of the smaller diameter microcapsules of the invention is in in-vivo uses, the living tissue-containing microcapsules may also be put to a variety of in-vitro uses.

In addition to producing microcapsules containing living tissue or cells, the present invention may be used to form microcapsules containing a variety of other core materials, depending on the intended end use of the microcapsules.

EXAMPLES

EXAMPLE 1

This Example illustrates the formation of small diameter gel droplets using an electrostatic droplet generator.

An apparatus as illustrated in FIG. 1 was set up. A 1.5% w/v sodium alginate solution (14) was placed in a 10 cc syringe (12) to which is attached a 22 gauge stainless steel needle (22) having a 90° bevel outlet. The positive polarity wire (28) was attached to the metal leur lock section of the needle and the needle-syringe combination was attached to the syringe pump (18). A 1.1% calcium chloride solution (26) was poured into a 4"×1" petri dish (24) to which was attached the negative polarity wire (30). The petri dish (24) was positioned so that the liquid surface therein was 10 mm from the tip of the needle (22).

The pulse voltage dial (122) on the adjustment panel (116) was set at 12 KV, the pulse frequency dial (118) at 20 sec$^{-1}$, the pulse length dial (120) at 2 m. sec, and the syringe pump speed at 4 ml/hr. The syringe pump (18) and droplet generator were both turned on so that sodium alginate liquid droplets (20) were drawn from the tip (27) of the needle (22) and, upon entering the calcium chloride solution in the petri dish (24), calcium alginate gel droplets were formed and were collected therein. The resultant calcium alginate gel droplets were found to be perfectly smooth and spherical and with a mean diameter of 300 ($\pm$50 SD) $\mu$m.

The syringe needle (22) used in this Example was of the same diameter as was previously used in an air jet syringe wherein a rapidly flowing air stream was used to remove sodium alginate liquid droplets from the tip (27) of the needle (22) using the air jet syringe, the smallest diameter calcium alginate gel droplets attainable had a diameter of 700 $\mu$m. The electrostatic procedure described in this Example, therefore, was able to decrease the gel droplet diameter to approximately half this value.

EXAMPLE 2

This Example illustrates the formation of small diameter gel droplets using an alternative form of droplet generation.

The procedure of Example 1 was repeated, except that the apparatus of FIG. 2 was utilized, i.e. the negative polarity wire (30) was attached to the needle (22) and the positive polarity wire (28) is attached to the metal ring device (32) which is spaced downwardly from the tip of the needle (22). The centre of the metal ring (32) was positioned 7 mm downwardly from the tip (27) of the needle (22) and an uncharged petri dish (24) was positioned about 5 cm downwardly from the ring assembly.

The calcium alginate gel droplets produced by this procedure and collected in the petri dish were observed to be perfectly smooth and spherical and to have a mean diameter of 450 ($\pm$65 SD) $\mu$m. When the experiment was repeated with the charge reversed, a greater variation of gel droplet diameter was observed with the standard deviation (SD) of gel droplet diameter approximately doubling.

EXAMPLE 3

This Example illustrates the viability of living tissue after passage through the electrostatic droplet generator.

The procedure of Example 1 was repeated except that islets of Langerhans extracted from the pancreatic tissue of dogs were added to the sodium alginate solution in the syringe in a concentration of 500 islets/2 ml and the calcium chloride solution was replaced by saline, so that gel droplet formation did not occur in this experiment. After passage through the electrostatic droplet generator, 100% of the islets were shown to be viable using Trypan blue staining. All the islets appeared white when viewed under the microscope, there being no evidence of the blue appearance characteristic of dead islets.

EXAMPLE 4

This Example illustrates the formation of small semipermeable microcapsules containing islets of Langerhans.

Cultured rat islets of Langerhans ($2 \times 10^3$ islets in 0.2 ml medium) were suspended uniformly in 2 ml of a 1.5% (2/2) sodium alginate solution (viscosity 51 cps) in physiological saline. Spherical droplets containing islets were produced with an electrostatic droplet generator using the procedure of Example 1 and were collected in 1.5% (w/w) calcium chloride solution. The supernatant was decanted and the gelled spherical calcium alginate droplets, containing islets, were washed with CHES (2-cyclohexylaminoethane sulfonic acid) solution and 1.1% calcium chloride solution.

After aspirating off the supernatant, the gelled droplets were incubated for 6 minutes in 0.05% (w/w) solution of polylysine having a molecular weight of 17,000. The supernatant was decanted and the polylysine capsules were washed with dilute CHES, 1.1% calcium chloride solution and physiological saline.

The washed polylysine capsules were incubated for 4 minutes in 30 ml of 0.03% sodium alginate to permit the formation of an outer alginate membrane on the initial polylysine membrane, by ionic interaction between the negatively-charged alginate and the positively-charged polylysine.

The resulting microcapsules were washed with saline, 0.05M citrate buffer for 6 minutes to reliquify the inner calcium alginate, and a final saline wash. The microcapsules were found to be perfectly spherical and each to contain from 1 to 2 viable islets. The microcapsules had a mean diameter of 300 ($\pm$50 SD) microns and wall thicknesses of 5 $\mu$m. The microcapsules were suspended in nutrient medium at 37° C.

The viability of the islets was demonstrated by Trypan Blue staining after the capsule walls were dissociated with heparin.

EXAMPLE 5

This Example illustrates the formation of small semipermeable microcapsules containing hepatocytes (liver cells).

The procedure of Example 4 was repeated except that fetal mouse or adult rat hepatocytes were added to the sodium alginate solution in amounts of $10^5$ hepatocytes/ml of alginate solution and the distance from the tip of the needle to the surface of the calcium chloride solution was decreased to 7 mm. The resulting microcapsules were spherical in appearance and had a diameter of 250 μm (±50 SD). The presence of viable hepatocytes was demonstrated by Trypan Blue staining and histology, even after more than 4 weeks in culture at 37° C.

EXAMPLE 6

This Example illustrates the effect of needle parameters on gel droplet size.

The procedure of Example 1 was repeated, except that a 26 gauge needle having a 22-degree bevel was used in place of the 22 gauge needle having the 90-degree bevel. The resultant gel droplets had a diameter of 170 μm (±30 SD), demonstrating the smaller diameter gel droplets and consequently microcapsules can be formed by using a smaller diameter needle.

SUMMARY OF DISCLOSURE

In summary of this disclosure, the present invention provides a novel droplet generation procedure using electrostatic forces which is particularly useful in the microencapsulation of living tissue or cells to form small diameter microcapsules suitable for cardiovascular injection. Modifications are possible within the scope of the invention.

What we claim is:

1. A composition of spherical, smooth and uniform microcapsules suitable for cardiovascular injection into an animal body, said microcapsules comprising:
    a core comprising one or more viable, healthy, physiologically-active tissue cells capable of on going metabolism and an aqueous medium of nutrients sufficient to maintain said tissue cells and allow normal metabolism thereof, and
    a biocompatible semi-permeable membrane surrounding and enclosing said core, said semi-permeable membrane being permeable to tissue nutrients and metabolic products produced by the tissue but impermeable to immune system proteins,
    said membrane comprising ionically-interacted biocompatible materials and having a negatively-charged outer surface, said microcapsules having a diameter consisting essentially of about 150 to about 500 microns.

2. The microcapsule composition of claim 1 wherein said tissue cells are islets of Langerhans, whereby said cardiovascular injection permits control of blood sugar levels in the animal body.

3. The microcapsule composition of claim 1 wherein said membrane has a thickness of about 4 to about 6 microns.

4. The microcapsule composition of claim 2 wherein said islets are entrapped within a reliquifiable reversible gel material.

5. The microcapsule composition of claim 4 wherein said reversible gel material is calcium alginate.

6. The microcapsule composition of claim 2 wherein said islets are entrapped within reliquified gel material.

7. The microcapsule composition of claim 6 wherein said reliquified gel material is aqueous sodium alginate.

8. The microcapsule composition of claim 1 wherein said semi-permeable membrane is formed about each of the microcapsules by ionic reaction between free acid groups in the surface layer of the gelled reversible gel material and a biocompatible polymer containing acid-reactive groups.

9. The microcapsule composition of claim 8 wherein said biocompatible polymer is a polyamino acid.

10. The microcapsule composition of claim 9 wherein the polyamino acid is a polylysine having a molecular weight of about 10,000 to about 30,000.

11. The microcapsule composition of claim 9 wherein said negatively-charged surface is provided by reacting the biocompatible polymer, after reaction with the gelled reversible gel material, with a non-toxic biocompatible water-soluble polymeric material capable of ionic reaction with free amino groups.

12. The microcapsule composition of claim 11 wherein said polymeric material is a polysaccharide gum.

13. The microcapsule composition of claim 12 wherein said polysaccharide gum is sodium alginate.

14. The microcapsule composition of claim 10 wherein said membrane has a thickness of about 4 to about 6 microns.

15. A method of controlling blood sugar levels in diabetic animals, which comprises:
    cardiovascularly injecting an effective amount of biocompatible, spherical and smooth microcapsules each having a diameter consisting essentially of from about 150 to about 500 microns,
    said microcapsules each having (1) a core comprising one or more viable, healthy, physiologically-active islets of Langerhans capable of on-going metabolism to produce insulin and a medium sufficient to maintain said islets of Langerhans and allow normal metabolism thereof and (2) a biocompatible semi-permeable membrane surrounding and enclosing said core, said semi-permeable membrane being permeable to nutrients for the islets and insulin produced thereby but impermeable to immune system proteins, said membrane comprising ionically-interacted biocompatible materials and having a negatively-charged outer surface.

16. The method of claim 15 wherein said semi-permeable membrane has a thickness of about 4 to about 6 μm.

17. The method of claim 15 wherein said medium is a reversible calcium alginate gel material in which at least one islet is suspended.

18. The method of claim 15 wherein said medium is an aqueous medium alginate solution containing nutrients for said islets and in which at least one islet is suspended.

* * * * *